United States Patent [19]

Little

[11] Patent Number: 5,005,584
[45] Date of Patent: Apr. 9, 1991

[54] FIBER OPTIC PRESSURE TRANSDUCER

[75] Inventor: Richard L. Little, New Hope, Minn.

[73] Assignee: MNM Enterprises, Inc., Minneapolis, Minn.

[21] Appl. No.: 461,178

[22] Filed: Jan. 5, 1990

Related U.S. Application Data

[63] Continuation of Ser. No. 62,728, Jun. 15, 1987, abandoned.

[51] Int. Cl.$^5$ .......................... A61B 5/00; A61B 5/02; A61M 25/00; C01L 7/08
[52] U.S. Cl. .................................... 128/748; 128/667; 128/675; 604/282; 73/715
[58] Field of Search .............................. 128/664–667, 128/672–675, 748, 634, 772; 73/705, 708, 715; 604/282

[56] References Cited

U.S. PATENT DOCUMENTS

| | | | |
|---|---|---|---|
| 3,686,958 | 8/1972 | Porter et al. | 128/748 |
| 4,611,600 | 9/1986 | Cohen | 128/667 |
| 4,645,343 | 2/1987 | Stockdale et al. | 356/326 |
| 4,676,249 | 6/1987 | Arenas et al. | 128/772 |

Primary Examiner—Max Hindenburg
Assistant Examiner—Robin R. Longo
Attorney, Agent, or Firm—Moore & Hansen

[57] ABSTRACT

A fiber optic transducer utilizing a flexible membrane to transduce pressure by interrupting light transmission between fiber optic paths in a catheter or guide wire carrier by misaligning the paths or by interposing a blocking opaque shutter between the paths. Calibration data may be carried by the individual transducer in machine readable form.

23 Claims, 3 Drawing Sheets

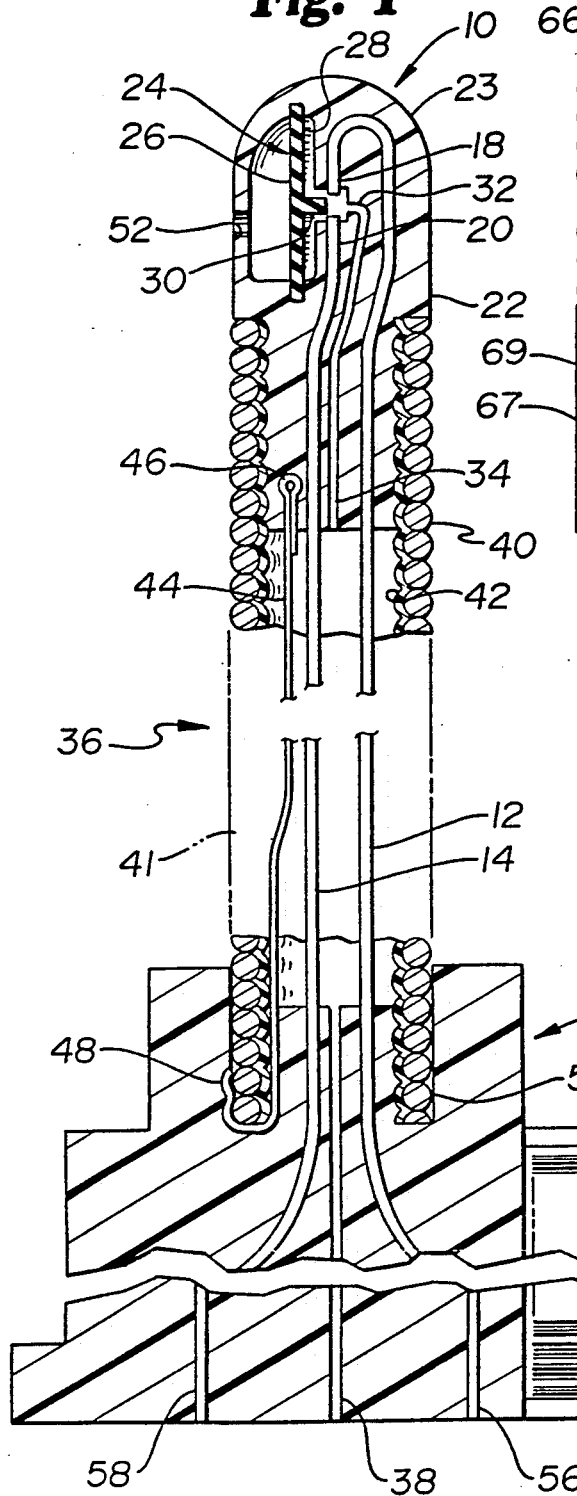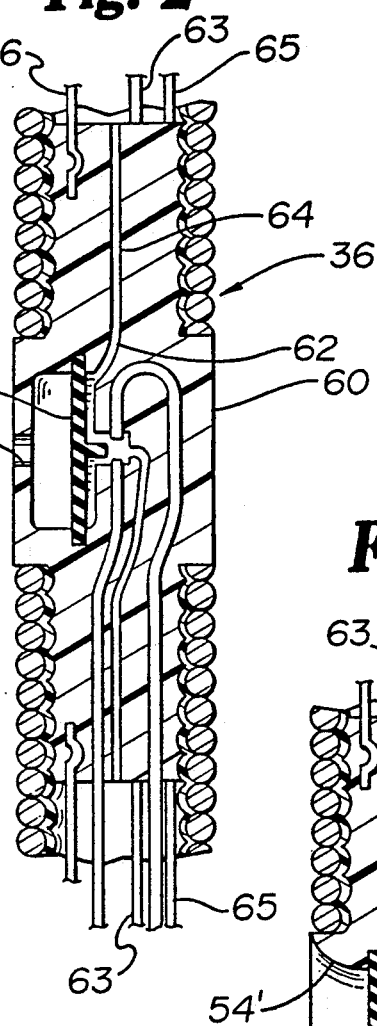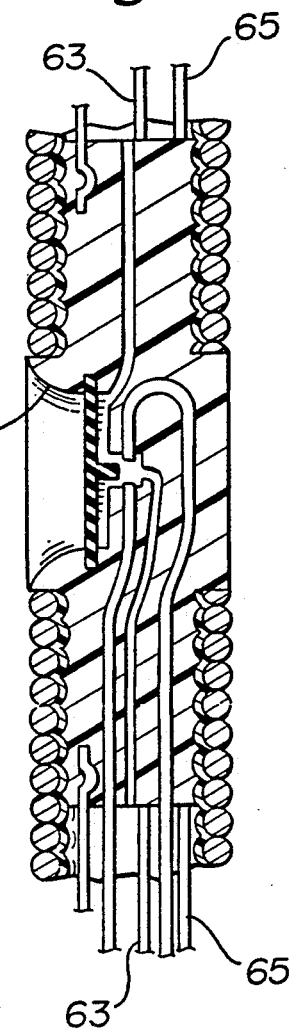

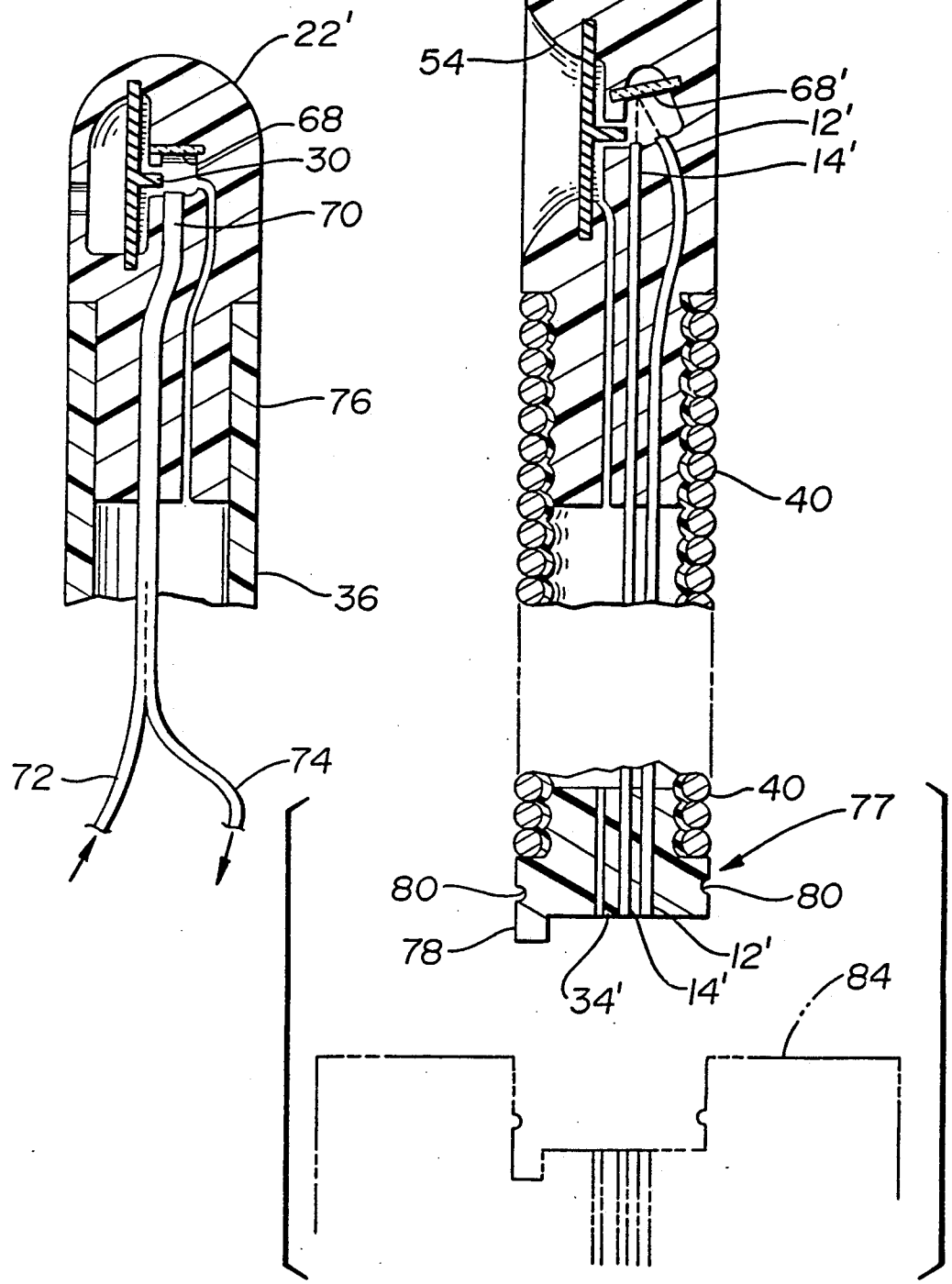

FIBER OPTIC PRESSURE TRANSDUCER

This is a continuation of application Ser. No. 062,728, filed June 15, 1987, abandoned.

BACKGROUND OF THE INVENTION

In the past, pressure transducer assemblies utilizing fiber optics generally required relatively complex geometries within the transducer, and further, required relatively complex interfacing circuitry to compensate for the non-ideal characteristics of such transducers.

The present transducer assembly provides for a relatively simple and low cost transducer which is extremely small and which may carry individualized calibration data.

BRIEF DESCRIPTION OF THE DRAWINGS

FIG. 1 shows a first embodiment of the pressure transducer of the present invention mounted at the end of a guide wire assembly.

FIG. 2 shows the pressure transducer of the present invention located in a mediate region of the guide wire assembly.

FIG. 3 shows an alternative embodiment of the pressure transducer of the present invention.

FIG. 4 shows a further alternative embodiment of the pressure transducer of the present invention.

FIG. 5 shows a still further alternative embodiment of the pressure transducer of the present invention.

DETAILED DESCRIPTION

Figure 6:
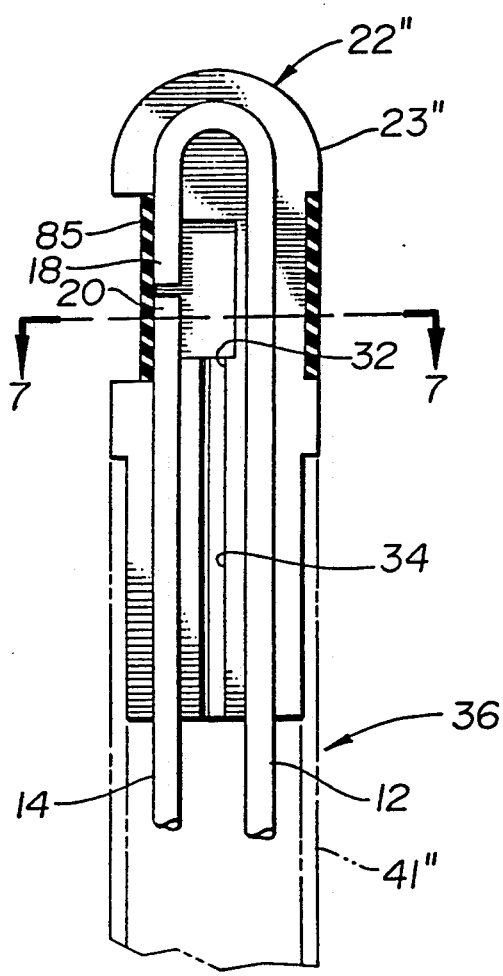
FIG. 6 shows a still further alternative embodiment of the pressure transducer of the present invention.

Referring now to FIG. 1, an improved physiological pressure transducer assembly 10 may be seen. This pressure transducer assembly is of the type which has extended fiber optic paths or channels 12, 14, one of which is suitable for light transmission to the transducer 10 and one of which is suitable for a signal transmission from the transducer through a connector 16 to appropriate interfacing equipment (not shown). Proximal ends 18, 20 of paths 12, 14 are located within a pressure transducer 22. Paths 12, 14 form a part of a transmission path or means from transducer 22 to connector 16.

Transducer 22 has a housing 23 preferably made of a rigid plastic which is bio-compatible, such as polyurethane. Alternatively, housing 23 may be formed of metal such as stainless steel. Transducer 22 further has a flexible membrane or pressure responsive deflection member 24 which has an exterior portion or surface 26 to sense pressure changes at transducer 22. Membrane 24 also has an interior portion or surface 28. In this embodiment membrane 24 further carries an opaque shutter 30, which may be formed integrally with membrane 24 at interior portion 28. Membrane 24 is preferably formed of relatively flexible polyurethane or silicone rubber or alternatively may be formed of any other bio-compatible material which provides sufficient flexibility to elastically deform or deflect in a repeatable manner in response to pressure changes encountered in the environment in which this transducer is to be used.

A vent 32 connects interior portion 28 of membrane 24 to a duct 34 forming part of transmission means 36 which preferably includes a generally tubular extended passageway. A second duct 38 may be formed in connector 16 to vent interior portion 28 to atmospheric pressure. Alternatively, an aperture in a side wall 41 of transmission means 36 remote from transducer 22 may provide that function.

In FIG. 1, transducer 22 is shown mounted at a proximal end of a coiled or helical guide wire 40 which forms an exterior structural wall 41 for transmission means 36. Guide wire 40 is preferably coated with a silicone rubber or polyurethane coating 42 which forms a relatively gas-tight, continuous imperforate barrier to maintain any pressure differential sensed between the exterior and interior of transducer assembly 10. Coating 42 also prevents the entry of foreign materials into transmission means 36 and transducer 22. In FIG. 1, coating 42 is shown interior of wire 40. Alternatively, coating 42 may be applied to the exterior of guide wire 40. As a still further alternative, coating 42 may be an impregnation of guide wire 40, effectively coating both the interior and exterior surfaces thereof. A safety wire 44 may be provided to aid in the withdrawal of assembly 10. In such event, a proximal end 46 of safety wire 44 preferably has an enlarged or other suitable anchoring configuration retained in a portion of transducer 22, preferably in housing 23. Distal end 48 of guide wire 44 is preferably secured to the distal end 50 of guide wire 40, by welding or other suitable connection. A physiologic pressure port or aperture 52 is preferably formed in housing 23 of transducer 22 to permit contact between exterior portion 26 of membrane 24 and the medium in which Pressure is to be sensed by transducer 22. Port 52 may comprise one or more relatively small apertures as shown in FIG. 1, or, alternatively, may comprise a relatively large opening or aperture 54 as shown in FIG. 5.

The operation of transducer 22 of this embodiment is as follows. In FIG. 1 membrane 24 is shown at rest and sensing a zero relative pressure between exterior portion 26 and interior portion 28. In the event of an increase in pressure at exterior portion 26 relative to interior portion 28 (and hence relative to atmospheric pressure) membrane 24 will elastically deform, moving shutter 30 to partially or completely block light transmission between proximal ends 18, 20 of fiber optic paths 12, 14. The change in light transmitted may be detected by external equipment connected to distal ends 56, 58 of paths 12, 14. It is to be understood that shutter 30 preferably proportionally blocks light transmission in response to a differential pressure across membrane 24.

Referring now to FIG. 2, an alternative embodiment may be seen. In this embodiment pressure transducer 60 is formed in a mediate portion of transmission means 36. Utilizing such a construction would Permit more than one transducer to be used in assembly 10. In the event that more than one transducer is to be used in the same assembly, it is to be understood that a second vent 62 and second duct 64 is preferable to provide access to atmospheric pressure for one or more transducers spaced apart from transducer 60. Additional fiber optic paths 63, 65 are provided when another transducer is to be used in the same assembly. One or more additional safety wires such as that shown at 66 may also be provided. As in FIG. 1, one or more ports 67 provide access to the pressure to be sensed by a membrane 69.

Referring now more particularly to FIG. 3, a further embodiment of transducer 60 may have an enlarged opening 54' similar to that shown for the transducer of FIG. 5.

Referring now more particularly to FIG. 4, a still further embodiment of a pressure transducer of the present invention may be seen. In this embodiment, a reflector 68 of suitable material, such as stainless steel or rigid plastic having an aluminum or other highly reflective metallic coating applied by vacuum deposition or other suitable processing is positioned to reflect light emitted from a first portion 72 of a fiber optic bundle 70 back to a second portion 74 of bundle 70. It is to be understood that portion 72 of bundle 70 serves to transmit light to transducer 22', while portion 74 serves to return light from transducer 22'. In this embodiment, shutter 30' preferably proportionally interrupts or blocks light transmission from portion 72 to portion 74 of bundle 70. It may be noted that in this embodiment, the proximal ends of the fiber optic paths are adjacent each other in bundle 70 in contrast to the embodiments shown in FIGS. 1-3 in which the proximal ends of fiber optic paths are in opposed spaced relationship to each other.

Also now referring to FIG. 4, the exterior wall of transmission means 36 may alternatively be formed by a catheter 76 which may be a suitable biologically compatible material, such as polyethylene or polyurethane, in either a homogenous wall construction as shown or in a composite wall construction, for example, a reinforced wall construction which uses a braided fiberglass or stainless steel woven layer in combination with one or more solid material layers. It is to be understood that in each alternative embodiment transmission means 36 includes the fiber optic paths to and from the transducer, exemplified by bundle 70 in FIG. 4.

Referring now more particularly to FIG. 5, in a still further embodiment, separate fiber optic paths 12', 14' may be utilized with a reflector 68'. It is to be understood that in this embodiment paths 12', 14' have proximal ends which are generally adjacent each other. The assembly of FIG. 5 further includes a connector 77 which is an alternative to connector 16. Connector 77 is no larger in diameter than guide wire 40. Connector 77 continues paths 12', 14' and provides for a vent or duct 34'. Connector 77 also preferably has a key 78 to orient connector 77 so as to properly orient paths 12', 14'. Connector 77 may also have a recess or a plurality of detents 80 to retain connector 77 in a mating receptacle 84 (shown in phantom). Receptacle 84 may be a relatively larger connector such as the connector 16 of FIG. 1 or may be a mating socket in equipment which utilizes the optical signal of the transducer. Utilizing small connector 77 permits unrestricted use of guide wire 40 in medical techniques which call for passage of a guide wire through other medical devices (such as a catheter). Although shown in FIG. 5, the alternative connector 77 may be utilized with any pressure transducer embodiment of this invention.

In the embodiments of FIGS. 1-5 it is to be understood that the proximal ends of the fiber optic paths are arranged in an optical coupling Path which light blocking shutter 30 interrupts in response to pressure-induced deflection of membrane 24.

Figure 7:
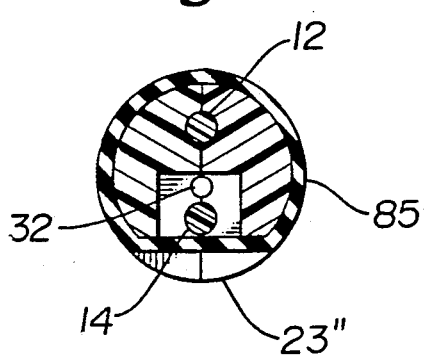
FIG. 7 shows a section view of the transducer of FIG. 6 taken along line 7—7'.

Referring now more particularly to FIGS. 6 and 7, a still further embodiment illustrates an alternative construction of pressure transducer 22". In this embodiment membrane 85 is formed of an elastic material which is generally cylindrical in its relaxed state, such as a section of tubing. Fiber optic paths 12, 14 are mounted in a cantilever fashion in relatively rigid housing 23". Proximal ends 18, 20 of paths 12, 14 are preferably in an opposed, spaced and coaxial position with respect to each other as shown in FIG. 6 when there is no change in pressure between the exterior and interior of housing 23. When a pressure change between the exterior and interior of housing 23 is sensed, membrane 85 will deform, moving proximal ends 18, 20 out of coaxial alignment, reducing light transmission therebetween, preferably in proportion to the pressure differential sensed between the interior and exterior of transducer 22". Transmission means 36 preferably includes exterior wall 41", and may include a safety wire (not shown).

Figure 8:
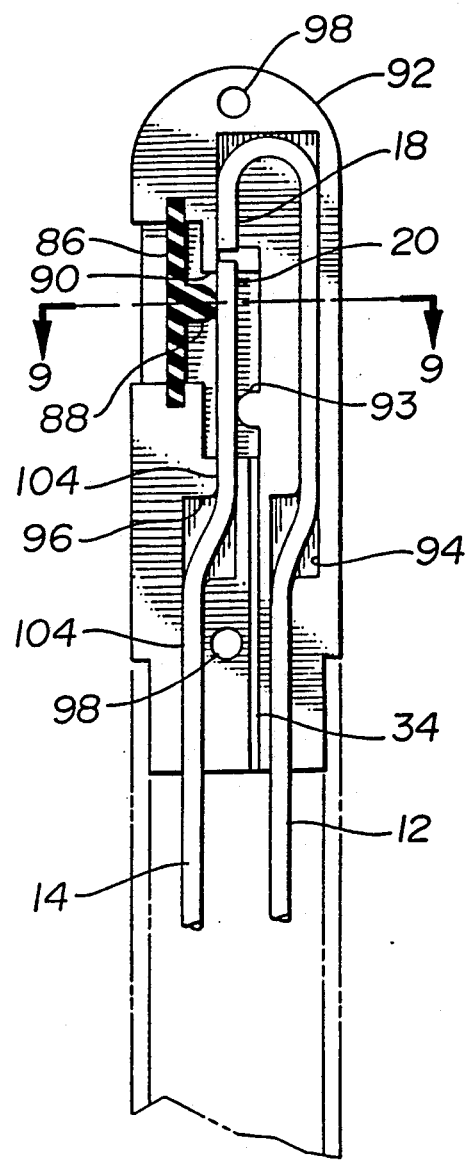
FIG. 8 shows a still further alternative embodiment of the pressure transducer of the present invention.
Figure 9:
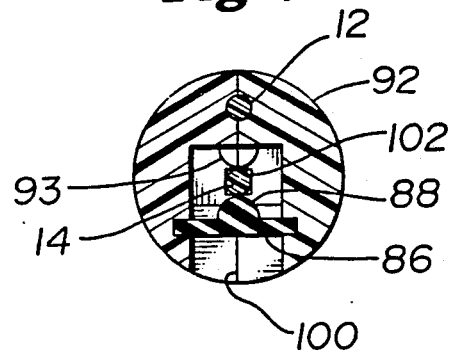
FIG. 9 shows a section view of the transducer of FIG. 8 taken along line 9—9'.

Referring now more particularly to FIGS. 8 and 9, a still further embodiment of the pressure transducer of this invention may be seen. In this embodiment, membrane 86 has a projection 88 on an interior portion thereof. Projection 88 rests against fiber optic path 14 near proximal end 20. Proximal ends 18, 20 rest against and are preferably coaxially aligned by portion 90 which itself is preferably formed as a part of relatively rigid housing member 92. It has been found preferable to have an additional projection 93 formed as a part of housing 92 to position proximal end 20 against portion 90. One or both fiber optic paths 12, 14 may be realigned within housing 92 by guide channels 94, 96. A duct 34 provides a passageway to the interior of housing 92 to allow membrane 86 to deform in response to pressure changes between the exterior and interior of housing 92. Alternatively, duct 34 may be formed as a rectangular or other non-conforming cross-sectional shape 102 for the channel or recess 104 in housing 92 carrying one or both fiber optic filaments or bundles. For example, by carrying a round fiber optic filament 14 in a square channel 104, a duct will exist along side filament 14 to the interior of membrane 86. Housing 92 may further have projections 98 and mating receptacles (not shown) extending out of the plane of parting line 100 between mating halves of housing 92 to locate the halves positively with respect to each other.

Referring now again to FIG. 1, connector 16 may have a bar code or other machine readable format label or indicia 82 affixed thereto such that assembly 10 carries individual calibration data if necessary to compensate for zero-offset, slope, and linearity anomalies which may be present in transducer 22. Alternatively, label 82 may be in magnetic format, e.g., a magnetic strip, carrying such calibration data.

To calibrate transducer 22, the transducer is first placed in a zero differential pressure condition across membrane 24, and the optical signal output from the transducer is observed and recorded or retained by equipment to which assembly 10 is connected through connector 16. Transducer 22 is then placed in a known non-zero pressure chamber such that the transducer is sensing a known pressure differential. While the transducer 22 is sensing the known pressure, the signal output from the transducer is observed and retained. This process may be repeated as many times as desired to obtain data points for inclusion in the calibration data on label 82 as a part of the manufacturing process.

Subsequently, when it is desired to put the transducer in use the calibration data for assembly 10 is read from label 82 and applied by equipment to which assembly 10 is connected to correct the output of transducer 22 during operation. In the event connector 77 is utilized with transducer of this invention, label 82 may be affixed to receptacle 84 or to the packaging of the transducer or to guide wire 40 or other transmission means 36 as by way of an adhesive-edged flag which is detachable from the guide wire after calibration data is read in connection with the use of transducer.

The invention is not to be taken to be limited to all of the details thereof as modifications and variations thereof may be made without departing from the spirit or scope of the invention. For example, the shutter 30 of membrane 24 may be positioned to completely block light transmission between ends 18, 20 with zero pressure differential across membrane 24, and shutter 30 may have an aperture or other open geometry which proportionally reduces blockage of light transmission as the pressure differential increases.

What is claimed is:

1. A combination of a transvenously insertable guide wire, with a physiological pressure transducer assembly of the type having extended fiber optic paths for light transmission to and from the transducer, the combination comprising:

an elongated guide wire comprised of multiple coils of wire defining an elongated tubular passage, said guide wire being sufficiently flexible to bend sharply as required in traversing a patient's vascular system;

a pair of fiber optic paths contained within said tubular passage of said guide wire and extending longitudinally therein inside of said coils, each of said fiber optic paths having a proximal and a distal end; and a pressure transducer mounted on said guide wire at the proximal ends of said fiber optic paths, said transducer comprising a housing within which the proximal ends of said fiber optic paths terminate adjacent to each other in optical coupling relation, said housing being at least partially contained within said guide wire in restraining engagement between opposite sides thereof, and a flexible membrane means having an exterior portion exposed to sense pressure exterior of said housing and an interior portion positioned to interrupt light transmission between the proximal ends of said fiber optic paths due to movement of said membrane in response to changes in pressure exterior of said housing, said pressure transducer having a lateral dimension no greater than that of said guide wire on which it is mounted.

2. The transducer assembly of claim 1 wherein said membrane means proportionally interrupts light transmission in response to said pressure change.

3. The transducer assembly of claim 2 wherein said pressure change is a pressure increase.

4. The transducer assembly of claim 1 wherein said membrane means further comprises a light transmission blocking means.

5. The transducer assembly of claim 4 wherein said blocking means comprises an opaque shutter which moves to block light transmission between said proximal ends of said fiber optic paths in response to said pressure changes.

6. The transducer assembly of claim 5 further comprising a reflecting means for reflecting light emitted from the proximal end of one of said fiber optic paths to the proximal end of the other of said fiber optic paths.

7. The transducer assembly of claim 6 wherein said proximal ends are in spaced, side-by-side, relationship to each other.

8. The transducer assembly of claim 1 wherein said proximal ends are in opposed relationship to each other.

9. The transducer assembly of claim 1 wherein said proximal ends are substantially coaxially aligned with each other when there is no change in pressure between the exterior and interior of said housing.

10. The transducer assembly of claim 9 wherein said membrane is in such juxtaposition with respect to said proximal ends as to deflect one of said proximal ends with respect to the other proximal end in response to a change in said pressure.

11. The transducer assembly of claim 9 wherein said membrane is in such juxtaposition with respect to said proximal ends as to deflect both proximal ends out of coaxial alignment with each other in response to said pressure change.

12. The transducer assembly of claim 1 wherein said membrane is formed of elastic material and is generally cylindrical in its relaxed state.

13. The transducer assembly of claim 1 wherein said guide wire is helical and carries a continuous imperforate barrier along its length.

14. The transducer assembly of claim 13 wherein said barrier is a coating interior of said guide wire.

15. The transducer assembly of claim 13 wherein said barrier is a coating exterior of said guide wire.

16. The transducer assembly of claim 1 and further including connector means for connecting to said distal ends of said fiber optic paths, said connector means being no larger in diameter than the exterior diameter of said guide wire.

17. The transducer assembly of claim 16 wherein said connector means further comprises orientation means for orienting the distal ends of said fiber optic paths to equipment external of the transducer assembly, wherein said orientation means comprises a key on said connector.

18. The transducer assembly of claim 1 further comprising venting means for permitting atmospheric pressure to reach the interior portion of said membrane, said venting means comprising a duct extending within said pressure transducer housing between said interior portion of said membrane and said elongated tubular passage of said guide wire.

19. The transducer assembly of claim 18 and further including a connector on one end of said elongated guide wire through which said distal ends of said fiber optic paths extend for connection to apparatus externally of said transducer assembly, said venting means further comprising a duct extending through said connector and communicating with the atmosphere externally of said connector.

20. The transducer assembly of claim 1 further comprising indicia affixed thereto and carrying individual calibration data for that respective transducer assembly.

21. The transducer assembly of claim 20 wherein said indicia comprises a bar code.

22. The transducer assembly of claim 20 wherein said indicia comprises a magnetic strip.

23. The transducer assembly of claim 1 wherein said transducer housing has the general shape of a cylinder, the diameter of which comprises said lateral dimension.

* * * * *